(12) United States Patent
Wu

(10) Patent No.: US 8,614,066 B2
(45) Date of Patent: Dec. 24, 2013

(54) METHOD OF USING LIGAND-FREE LYSING AGENT IN HEMOGLOBIN ANALYSIS

(75) Inventor: Jiong Wu, Los Gatos, CA (US)

(73) Assignee: Abbott Laboratories, Abbott Park, IL (US)

( * ) Notice: Subject to any disclaimer, the term of this patent is extended or adjusted under 35 U.S.C. 154(b) by 377 days.

(21) Appl. No.: 12/855,878

(22) Filed: Aug. 13, 2010

(65) Prior Publication Data

US 2011/0053206 A1 Mar. 3, 2011

Related U.S. Application Data

(60) Provisional application No. 61/236,976, filed on Aug. 26, 2009.

(51) Int. Cl.
*G01N 33/567* (2006.01)

(52) U.S. Cl.
USPC ............................ 435/7.21; 435/7.25

(58) Field of Classification Search
USPC .................................. 435/7.21, 7.25
See application file for complete search history.

(56) References Cited

U.S. PATENT DOCUMENTS

| | | | |
|---|---|---|---|
| 5,612,223 | A | 3/1997 | Kim et al. |
| 5,631,165 | A | 5/1997 | Chupp et al. |
| 5,866,428 | A | 2/1999 | Kim et al. |
| 5,939,326 | A | 8/1999 | Chupp et al. |
| 5,958,781 | A | 9/1999 | Wong et al. |
| 6,740,527 | B1 | 5/2004 | Wong et al. |
| 6,890,756 | B2 | 5/2005 | Wu |

FOREIGN PATENT DOCUMENTS

| | | |
|---|---|---|
| WO | WO 96/02841 A1 | 2/1996 |
| WO | WO 2009/150327 A2 | 12/2009 |

OTHER PUBLICATIONS

Tsuda et al. "Evaluation of Coulters cyanide-free reagent for hemoglobinometry", Laboratory Hematology, 1998, 4:276-280.* van Hove et al. "Anemia diagnosis, classification and monitoring using cell-dyn technology reviewed for the new millennium", Lab Hematol., 2000, 6:93-108.*

Lee et al. "Peroxiredoxin II is essential for sustaining life span of erythrocytes in mice", Blood, 2003, 101(12):5033-5038.*

CELL-DYN® Ruby. Abbott Diagnostics. Products [online]. [retrieved on Jul. 30, 2010] Retrieved from the Internet: <URL: http://www.abbottdiagnostics.com/Products/Instruments_by_Platform/>, 3 pages.

CELL-DYN® Sapphire. Abbott Diagnostics. Products [online]. [retrieved on Apr. 8, 2008] Retrieved from the Internet: <URL: http://www.abbottdiagnostics.com/Products/Instruments_by_Platform/>, 6 pages.

CELL-DYN® 3200. Abbott Diagnostics Products [online]. Abbott Laboratories, 2008 [retrieved on Apr. 8, 2008] Retrieved from the Internet: <URL: http://www.abbottdiagnostics.com/Products/Instruments_by_Platform/>, 3 pages.

Karsan A., et al., "An Evaluation of Hemoglobin Determination Using Sodium Lauryl Sulfate," American Journal of Clinical Pathology, 1993, vol. 100 (2), pp. 123-126.

Lewis S.M., et al., "Lauryl sulphate haemoglobin: a non-hazardous substitute for HiCN in haemoglobinometry," Clinical and Laboratory Haematology, 1991, vol. 13 (3), pp. 279-290.

Notification of Transmittal of the International Search Report and the Written Opinion of the International Searching Authority, or the Declaration for Application No. PCT/US2010/046127, mailed on Oct. 22, 2010, 16 pages.

Oshiro I., et al., "New Method for Hemoglobin Determination by Using Sodium Lauryl Sulfate (SLS)", Clinical Biochemistry, 1982, vol. 15 (1), pp. 83-88.

Salager, FIRP Booklet #E300-A, Surfactants, Types and Uses, Laboratory of Formulation, Interfaces, Rheology, and Processes, Universidad de Los Andes, Facultad de Ingenieria, Escuela de Ingenieria Quimica, merida-Venezuela, Version #2 (2002), pp. 1-49.

Theodorsen L., et al., "Automated cyanide-free method for haemoglobin determination on Technicon H•1," Scandinavian Journal of Clinical and Laboratory Investigation, 1990, vol. 50 (6), pp. 643-648.

\* cited by examiner

*Primary Examiner* — Bin Shen
(74) *Attorney, Agent, or Firm* — Edward J. Baba; Benjamin C. Pelletier; Bozicevic, Field & Francis LLP

(57) ABSTRACT

Lysing agents that are free of ligands, including cyanide, for binding hemoglobin for hematology analyzers. The ligand-free lysing agents achieve accurate quantification of hemoglobin parameters, thereby replacing existing lysing agents for analysis of hemoglobin.

27 Claims, 3 Drawing Sheets

METHOD OF USING LIGAND-FREE LYSING AGENT IN HEMOGLOBIN ANALYSIS

This application is a non-provisional application claiming priority from U.S. Provisional Application Ser. No. 61/236,976, filed Aug. 26, 2009.

BACKGROUND

1. Field of the Invention

This invention relates to lysing agents, more particularly, lysing agents for analysis of hemoglobin.

2. Discussion of the Art

The science of hematology has long recognized the importance of measuring the amount of hemoglobin in a blood sample, because it is the hemoglobin molecule that transports oxygen from the lungs to the various tissues and organs of the body. It can be argued that the accurate measurement of the concentration of hemoglobin in a patient's blood is the most important parameter in a hematology analysis. The concentration of hemoglobin is used to screen for anemia, which, in turn, is a sign of underlying disease.

A concentration of hemoglobin below 14 grams per deciliter (g/dL) in men and 12 g/dL in women is indicative of anemia. The causes of anemia are many, and a low concentration of hemoglobin is a strong signal for a thorough workup by a patient's physician. The two most common reasons for a patient to be anemic are blood loss and dietary deficiencies in iron, vitamin $B_{12}$, or folic acid. In the case of anemia, it is mandatory for the patient's physician to determine the cause of loss of blood and treat it. In the case of a vitamin deficiency or a mineral deficiency, a proper diagnosis is needed to determine the appropriate nutritional supplement(s).

In addition to its importance as the primary indicator of anemia, the concentration of hemoglobin is used in combination with other parameters of blood cells to calculate several indices. The value of mean corpuscular hemoglobin (MCH), which is the mass of hemoglobin per red cell, is calculated by dividing the concentration of hemoglobin by the concentration of red blood cells. The mean corpuscular hemoglobin concentration (MCHC) is the weight percent of hemoglobin in a red blood cell and is calculated by dividing the concentration of hemoglobin by the hematocrit and converting the quotient to a percent. Both MCH and MCHC are useful parameters in the diagnosis of anemia.

Modern methods of measuring the concentration of hemoglobin utilize spectrophotometry to quantify the amount of the oxygen-carrying protein in a sample of blood. The requirements of any spectrophotometric method are twofold:

(1) The method must release all the hemoglobin from the red blood cell in which it is sequestered.
(2) The method must convert all the hemoglobin in the sample into a single chromogenic species, regardless of the form in which the hemoglobin existed when the binding reaction between the ligand and protein began.

The first requirement can be achieved by diluting a sample of blood in distilled water to effect a hypotonic lysis. However, modern automated hematology analyzers require a more rapid lysis than can be achieved with hypotonic lysis. Frequently, surfactants are added to the lysing agent to hasten the release of hemoglobin and to clear any turbidity. Various classes of surfactants are suitable for this task, including anionic, non-ionic, zwitterionic, and cationic. The amount of surfactant required can range from about 100 mg/L to about 50 g/L, depending on the potency of the surfactant and other features of the lysing agent, such as, for example, pH, osmolality.

The second requirement necessitates an understanding of the chemistry of the heme iron, which carries oxygen when complexed in a globin protein molecule. The heme iron is maintained in the $Fe^{+2}$ oxidation state in a sample of normal blood. Because a sample of blood is usually drawn from a vein, the hemoglobin is usually in the deoxy state, i.e., no oxygen is bound to the heme iron. However, as soon as the sample comes into contact with the ambient air, or is introduced into an oxygen-containing buffer or lysing agent, the hemoglobin is rapidly converted into oxy-hemoglobin; the heme iron binds oxygen but stays in the $Fe^{+2}$ (reduced) state. In many cases, the amount of hemoglobin in the sample can be determined from the oxy-hemoglobin chromogen, which is formed naturally upon exposure of the sample to air. However, in some diseases, genetic conditions, or poisonings, a patient may have a significant amount of methemoglobin in circulation. In methemoglobin, the heme iron is in the $Fe^{+3}$ oxidized state. The heme iron cannot bind oxygen, nor can it be readily reduced to $Fe^{+2}$ so that the heme iron can bind oxygen to be measured as oxy-hemoglobin. Heavy cigarette smokers and workers exposed to high concentrations of automobile exhaust frequently accumulate a high concentration of carbon monoxide bound to their heme iron. Carbon monoxide is tightly bound and blocks the binding of oxygen, thereby causing an error in the measurement of the concentration of hemoglobin if the concentration of hemoglobin is determined by the oxy-hemoglobin method. The most commonly used approach for the measurement of hemoglobin is to oxidize all of the heme iron to the $Fe^{+3}$ oxidized state and to introduce a ligand that will quantitatively bind to all the heme iron in the $Fe^{+3}$ oxidized state to produce a single chromogenic species for quantification by spectrophotometry.

The classical method for measuring the concentration of hemoglobin is that of Drabkin. The hemoglobin is released from the sample of blood by hypotonic lysis, the heme iron is oxidized to the $Fe^{+3}$ oxidized state by means of potassium ferricyanide $[K_3Fe(CN)_6]$, and the iron is reacted with the cyanide anion of the potassium cyanide (KCN). Cyanide binds very tightly to $Fe^{+3}$ and gives a distinctive chromogen with a peak at a wavelength of about 540 nanometers (nm).

Traditional methods for analyzing hemoglobin employ (1) at least one quaternary ammonium salt as a lysing agent to destroy erythrocytes and (2) potassium cyanide (KCN) as a binding ligand to bring about rapid conversion of hemoglobin to the cyanomet-derivative of hemoglobin. The rapid binding of cyanide to hemoglobin and the extremely stable absorption spectrum of cyanmethemoglobin (peak $\epsilon = 12.5$ mM$^{-1}$ cm$^{-1}$ at a wavelength of about 540 nm) ensure accurate count of hemoglobin in a sample of whole blood and in a sample of control/calibrator.

However, the use of cyanide in a lysing agent raises safety and environmental concerns, and the handling and disposal of waste material is costly and presents risks to the environment. Yet, the cyanmethemoglobin method for analyzing hemoglobin is still deemed the most preferred method for analyzing hemoglobin.

Accordingly, a great deal of effort has been expended over the past twenty years to develop methods for analyzing hemoglobin without the need for using cyanide. The major suppliers in the hematology industry have adopted cyanide-free methods for analyzing hemoglobin in their state-of-the-art hematology analyzers. These cyanide-free methods for analyzing hemoglobin require using one or more binding ligands for hemoglobin in order to achieve equivalent absorbance at the typical measurement wavelength (540 to 560 nm). Cyanide-free methods have eliminated the cyanide reagent. See, for example, U.S. Pat. Nos. 5,631,165; 5,939,326; 5,612,223; 5,866,428; 5,958,781; 6,740,527; 6,890,756, all of which are incorporated herein by reference.

The methods described in U.S. Pat. Nos. 5,612,223 and 5,866,428 use a cyanide-free reagent comprising an aqueous solution of (i) a cyanide-free ligand selected from the group consisting of imidazole, imidazole derivatives, N-hydroxyacetamide, N-hydroxylamine, pyridine, oxazole, thiazole, pyrazole, pyrimidine, purine, quinoline, and isoquinoline and (ii) a strong erythrolytic surfactant selected from the group consisting of lauryl dimethylamine oxide and octylphenoxy ethanol. The pH of the reagent is adjusted to from about 11 to about 14, preferably with a monovalent base. According to the methods, the cyanide-free reagent is rapidly mixed with the blood sample to form a chromogen. The absorbance, or optical density, of the resulting chromogen is then measured to provide an indication of the concentration of hemoglobin. The methods described in U.S. Pat. Nos. 5,958,781 and 6,740,527 use a cyanide-free reagent comprising (1) at least one quaternary ammonium salt selected from the group consisting of tetradecyltrimethyl ammonium bromide, dodecyltrimethyl ammonium chloride, cetyl trimethyl ammonium bromide, hexadecyltrimethyl ammonium bromide, benzalkonium chloride, and cetyl pyridium chloride and (2) at least one hydroxylamine salt selected from the group consisting of hydrochloride, sulfate, phosphate, and other acid salts. A chromogen is formed, detected, and measured, thereby indicating concentration of hemoglobin in a sample of whole blood as well as white blood cell population and subpopulation determinations. The method described in U.S. Pat. No. 6,890,756 uses a cyanide-free lyse solution including a quaternary ammonium salt surfactant, an anionic surfactant, a hemoglobin binding agent selected from the group consisting of imidazole and hydroxylamine, and an aqueous medium.

However, the foregoing cyanide-free methods require the use of ligands for binding hemoglobin. These binding ligands are undesirable because of safety, health, and cost considerations. Accordingly, it would be desirable to develop simplified lysing agent formulations without the use of binding ligands.

SUMMARY OF THE INVENTION

This invention provides a method for analyzing hemoglobin by means of an automated hematology analyzer. The method involves the use of a combination of at least one lysing agent in the absence of binding ligands to control the level of turbidity in the reaction mixture in order to accurately determine the concentration of hemoglobin in a sample of whole blood. The method requires a composition comprising (a) a solvent and (b) at least one lysing agent. Optionally, the composition can include a diluent. The composition also requires the absence of ligands for binding hemoglobin. The absence of ligands for binding hemoglobin, such as, for example, cyanide, hydroxylamine HCl, imidazole, and other ligands, reduces harm to the environment, minimizes health-related risks, and lowers the cost of manufacture. Other factors for controlling the turbidity of the reaction mixture include adjusting of the concentration(s) of the at least one lysing agent and adjusting of the pH of the at least one lysing agent.

A combination of lysing agents, e.g., one or more quaternary ammonium salts, can be used to achieve optimal strength and effect of the ligand-free lysing agent described herein. Lysing agents suitable for use in this invention include, but are not limited to, quaternary ammonium salts, tertiary ammonium salts, quaternary amine oxides, tertiary amine oxides, and combinations of the foregoing.

The key to this invention is to properly control the strength of the ligand-free lysing agent and to allow the fragments of membranes of red blood cells to quantitatively contribute to the measured absorbance of the reaction mixture in order to match a selected absorbance target. The strength of the ligand-free lysing agent determines the length of time required to rupture membranes of red blood cells in a sample of whole blood. A strong lysing agent is a lysing agent that can rupture membranes of red blood cells in a short period of time, e.g., less than 10 seconds. A weak lysing agent is a lysing agent that ruptures membranes of red blood cells in a longer period of time, e.g., greater than 10 seconds. A strong lysing agent may leave a very low number of fragments of red blood cells at the time of measurement of hemoglobin; a weaker lysing agent would leave a higher number of fragments of red blood cells at the time of measurement of hemoglobin. The preferred strength of the ligand-free lysing agent is arbitrary. One of ordinary skill in the art can select the desired strength of the ligand-free lysing agent by means of trial-and-error without undue experimentation.

The ligand-free lysing agent approach described herein can be implemented and validated on the CELL-DYN® 3200 and CELL-DYN® Ruby hematology analyzers. The ligand-free lysing agent described herein provides results that match well with the existing hemoglobin (HGB)/nuclear optical count (NOC) lysing agents in terms of recoveries of hemoglobin.

Other benefits of the method described herein include (1) the elimination of cyanide, which is a hazardous material; (2) the elimination of imidazole, which is a costly material; (3) the elimination of hydroxylamine, which is very reactive and is considered an explosive.

DETAILED DESCRIPTION

Figure 1:
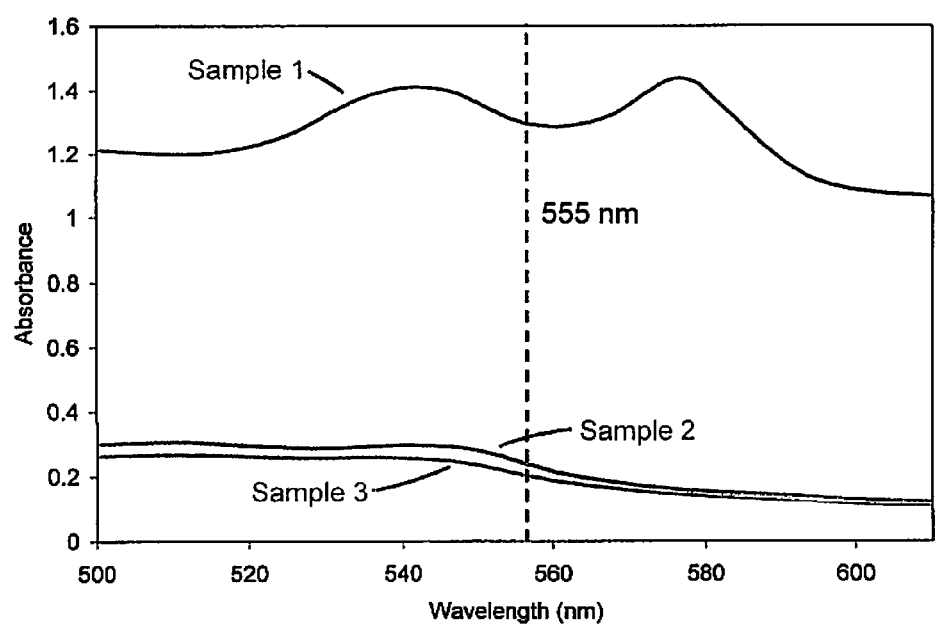
FIG. 1 is a graph illustrating absorbance as a function of wavelength for (a) Sample 1 of EXAMPLE 1, (b) Sample 2 of EXAMPLE 1, and (c) Sample 3 of EXAMPLE 1.

As used herein, the term "absorbance" is defined as $A_\lambda = -\log_{10}(l/l_0)$, where $l$ represents the intensity of light at a specified wavelength 2, that has passed through a sample (transmitted light intensity) and $l_0$ represents the intensity of the light before it enters the sample or incident light intensity (or power). As used herein the expression "molar absorptivity" means a measurement of how strongly a chemical species absorbs light at a given wavelength. It is an intrinsic property of the species, the actual absorbance, A, of a sample being dependent on the path length l and the concentration c of the species via the Beer-Lambert law, $A=\delta \times c \times l$.

As used herein, the term "methemoglobin" means hemoglobin containing $Fe^{3+}$. As used herein, the term "cyanmethemoglobin" means a tightly bound complex of methemoglobin with the cyanide ion. As used herein, the term "MCH" means mean cell hemoglobin. MCH is typically measured in units of picograms/cell. As used herein, the term "MCHC" means mean cell hemoglobin concentration. MCHC is typically measured in units of grams per deciliter.

As used herein, the expression "heme iron" means the iron atom contained in the center of the porphyrin moiety of hemoglobin. The iron atom is either $Fe^{+2}$ or $Fe^{+3}$.

As used herein, the term "hematocrit" means the proportion of blood volume that is occupied by red blood cells. Hematocrit is typically measured in units of percent (%).

As used herein, the expression "globin protein molecule" means the protein molecule folded into a globular form.

As used herein, the expression "deoxy state" means that the heme iron is $Fe^{+2}$ and no ligand, such as for example $O_2$ or $CO_2$, is bound to the heme iron.

As used herein, the expression "hemoglobin binding ligand" means the small molecule that can bind heme iron to form a complex. Examples of hemoglobin binding ligands include, but are not limited to, $O_2$, $CO_2$, CO, NO, F, $CN^-$.

As used herein, the expression "lysing agent" means a material that is capable of rupturing the membrane of a red blood cell. As used herein, the expression "ligand-free lysing agent" means a composition comprising at least one lysing agent, a solvent, and, optionally, a diluent.

As used herein, the expression "reaction mixture" means a mixture comprising at least one lysing agent, a solvent, and a sample of whole blood. Depending upon the method for carrying out an assay for hemoglobin and the hematology analyzer employed, the reaction mixture can also include a diluent.

The ability to measure the concentration of hemoglobin in a sample of blood is an essential part of hematology analysis. The level of hemoglobin is both a direct and an indirect indicator of many conditions associated with an inadequate level of hemoglobin in a patient.

The method described herein involves a method for analyzing hemoglobin by means of an automated hematology analyzer and a ligand-free lysing agent. The method involves the use of at least one lysing agent, free of any ligand for binding hemoglobin, to control the level of turbidity of a lysed sample of blood in order to obtain an accurate measurement of the concentration of hemoglobin in the lysed sample of blood. Representative classes of lysing agents suitable for use herein include, but are not limited to, quaternary ammonium salts, tertiary ammonium salts, quaternary amine oxides, tertiary amine oxides. The absence of binding ligands for hemoglobin, such as, for example, cyanide, hydroxylamine HCl, imidazole, and other ligands, reduces harm to the environment, minimizes health-related risks, and lowers the cost of manufacture.

In order to obtain an accurate measurement of hemoglobin for a sample of blood, a reaction mixture that achieves the desired absorbance at the specified wavelength (usually at 540 nm or slightly higher) is generated. The mixture must provide a molar absorptivity ($\epsilon$) in a range of 12.4 to 12.6 $mM^{-1}$ $cm^{-1}$ at a wavelength of 540 nm, assuming that cyanmethemoglobin is the reference method for a given hematology analyzer.

The ligand-free approach described herein ensures that all of the hemoglobin in the reaction mixture is in the ligand-free methemoglobin form, thereby exhibiting a lower level of molar absorptivity at a wavelength of 540 nm. The molar absorptivity of methemoglobin is also pH sensitive, but the molar absorptivity of methemoglobin is substantially lower than the target value. The selection of lysing agents (e.g., quaternary ammonium salts and other surfactants), as well as their concentrations, determines the quantity of the residual fragments of red blood cells (debris or stroma) remaining in the reaction mixture at the moment of the measurement of absorbance. The small fraction of fragments of red blood cells contributes to a higher level of turbidity and absorbance in the range of visible light, as indicated by the slightly cloudy appearance of the reaction mixture. The higher absorbance measurement resulting from fragments of residual red blood cells offsets the lower values of absorbance and molar absorptivity attributable to the pure methemoglobin.

For a given automated hematology analyzer, such as, for example, a CELL-DYN® 3200 hematology analyzer, the ligand-free lysing agent uses membranes from fragments of red blood cells to compensate for the reduction of desired absorbance on account of the absence of the ligand that binds hemoglobin. Of course, several parameters can be varied to develop the ligand-free lysing agent particularly desired. The key factor in developing the ligand-free lysing agent described herein is based upon a modified version of the Beer-Lambert law. According to this modified version of the Beer-Lambert law:

$$A_{Target} = [\epsilon(\text{met-Hb}) \times c \times l] + A_{RBC\ fragments}$$

where $A_{Target}$ represents the absorbance of the reference method $\epsilon(\text{met-Hb})$ represents molar absorptivity of methemoglobin c represents the concentration of methemoglobin l represents the light pass length $A_{RBC\ fragments}$ represents the contribution to the absorbance from fragments of red blood cells A constant, k, which is the ratio of $A_{RBC\ fragments}$ to $A_{Target}$ is specified for a given hematology analyzer. This ratio preferably ranges from about 0.01 to about 0.25. This ratio enables the $A_{RBC\ fragments}$ to compensate for the absence of ligands for binding hemoglobin in the ligand-free lysing agent composition that comprises the at least one lysing agent. The value of $A_{RBC\ fragments}$ is specified for a given hematology analyzer. The ligand-free lysing agent is formulated so that a suitable value of $A_{RBC\ fragments}$ is set and $A_{Target}$ is reached. This ligand-free lysing agent can be used with the hematology analyzer without the need for a ligand for binding hemoglobin. The ligand-free lysing agent can be prepared by dissolving a specific quantity of the at least one lysing agent in a solvent. In general, the solvent used to dissolve the salts is deionized water.

In general, it is preferred that at least 75%, more preferably 90%, and most preferably 95% of the absorbance of the reaction mixture be contributed by methemoglobin. Similarly, it is preferred that less than 25%, more preferably less than 10%, and most preferably less than 5% of fragments of red blood cells resulting from lysis of red blood cells contribute to absorbance of the reaction mixture.

The ligand-free lysing agent composition comprises (a) a solvent, (b) at least one lysing agent, and, optionally, (c) a diluent. If used, the function of the diluent is to dilute a sample of whole blood prior to determining the concentration of hemoglobin and the concentration of leukocytes. The concentration of leukocytes is typically determined with a separate lysing agent for white blood cells. The solvent is used to dissolve the lysing agent in an aqueous solution, if the lysing agent is a solid, or to dilute the lysing agent to the preferred concentration, if the lysing agent is a liquid, before the ligand-free lysing agent contacts red blood cells in the diluted whole blood sample. Typically, the diluent is an aqueous solution of an organic salt or an aqueous solution of an inorganic salt. The solvent is typically deionized water. As used herein, the term "diluent" means a well-buffered organic solution or inorganic solution, typically isotonic (250 to 350 mOsm) and typically neutral (pH ranging from about 6 to about 8. The diluent typically contains an anticoagulant, e.g., EDTA, and an antibacterial agent or an antifungal agent, or both an antibacterial agent and an antifungal agent, and other components that are desirable for hematological assays.

Lysing agents suitable for use in the ligand-free lysing agent include, but are not limited to: (1) quaternary ammonium salts, (2) tertiary ammonium salts, (3) quaternary amine oxides, and (4) tertiary amine oxides. Quaternary ammonium salts are salts of quaternary ammonium cations with an anion. Preferred anions are halogen anions, e.g., fluoride, chloride, bromide. Quaternary ammonium cations are positively charged polyatomic ions of the structure $NR_4^+$, each R being an organic radical substituted for a hydrogen of the original ammonium cation. Organic radicals that can be substituted for the hydrogens of the original ammonium cation can be alkyl, aryl, or aralkyl radicals. The nitrogen can be part of a ring system. Preferably, each R is an alkyl group. Unlike the ammonium ion ($NH_4^+$) and the primary, secondary, or tertiary ammonium cations, the quaternary ammonium cations are permanently charged. An amine oxide, also known as amine-N-oxide and N-oxide, is a chemical compound that contains the functional group $R_3N^+O^-$, i.e., an N—O bond having three additional hydrogen and/or hydrocarbon side chains attached to the nitrogen, N. $R_3$ can comprise (a) one hydrogen and two hydrocarbon side chains, (b) two hydrogens and one hydrocarbon side chain, (c) three hydrogens, or (d) three hydrocarbon side chains.

Preferred alkyl substituents linked to N for the quaternary ammonium salts, tertiary ammonium salts, quaternary amine oxides, and tertiary amine oxides include one or more carbon chains having from six to twenty (20) carbon atoms, more preferably from twelve (12) to twenty (20) carbon atoms.

Other surfactants that can be added to lysing agents suitable for use herein include anionic surfactants, such as, for example, sodium dodecyl sulfate (SDS), and non-ionic surfactants, such as those having the trademarks Triton® X-100 and Tween® 20. Anionic and non-ionic surfactants are discussed in, for example, Salager, FIRP Booklet #E300-A, SURFACTANTS, Types and Uses, Laboratory of Formulation, Interfaces, Rheology, and Processes, Universidad de Los Andes, Facultad de Ingenieria, Escuela de Ingenieria Quimica, merida-Venezuela, Version #2 (2002), pp. 1-49, incorporated herein by reference. Under some circumstances, it is possible to use an anionic or a non-ionic surfactant as the sole lysing agent in a ligand-free lysing agent, so long as the strength of the anionic or non-ionic surfactant is adequate. A combination of lysing agents can be used to increase the strength of the ligand-free lysing agent and enhance the effects of the ligand-free lysing agent. By increasing the strength of the ligand-free lysing agent, by, for example, adjusting concentrations of ammonium salts or amine oxides, the speed of lysing can be accelerated and the number of fragments of red blood cells can be reduced. This ligand-free approach described herein can be implemented and validated on the CELL-DYN® 3200 and CELL-DYN® Ruby hematology analyzers, both of which are commercially available from Abbott Laboratories. The ligand-free lysing agent described herein matches well with the existing hemoglobin/NOC lysing agents in terms of recoveries of hemoglobin.

The ammonium salt(s) or ammonium oxide(s), or anionic surfactant(s) or non-ionic surfactant(s) that can be substituted for ammonium salt(s) or ammonium oxide(s), should be present in the ligand-free lysing agent at a concentration ranging from about 0.01% to about 50%, preferably from about 0.1% to about 30%, more preferably from about 1% to about 20%, based on either weight or on volume. The specific concentration depends on the characteristics of the particular hematology analyzer and on the operational procedure in which the ligand-free lysing agent is employed. No ligand, such as, for example, hydroxylamine or imidazole or other heme iron binding moiety, should be incorporated into the ligand-free lysing agent.

In order to perform an assay to determine the concentration of hemoglobin, a sample of whole blood is treated with a diluent. A ligand-free lysing agent is prepared by dissolving a specific quantity of at least one quaternary ammonium salt or at least one quaternary amine oxide or at least one quaternary ammonium salt and at least one quaternary ammonium oxide and any other components in a solvent. The ligand-free lysing agent is mixed with the diluted sample of whole blood, and then the mixed sample is introduced to a hemoglobin flow cell (e.g., absorbance spectrophotometer) for the measurement of optical density at a wavelength of from about 540 to about 560 nm. The optical density measurements are then correlated to the concentration of hemoglobin. The result is reported as measured weight of hemoglobin per volume of whole blood.

The following non-limiting examples further illustrate the ligand-free lysing agent described herein.

Example 1

The purpose of this example is to demonstrate that a combination of free methemoglobin (>50%) and unlysed red blood cells or fragments of red blood cells (<50%) resulting from a ligand-free lysing agent can match the performance of a reference lysing agent for an analysis of hemoglobin. The free methemoglobin component exhibits low absorbance; the unlysed red blood cells or fragments of red blood cells exhibit high absorbance. In this example, the diluent used was the Diluent/Sheath for the CELL-DYN® Sapphire™, CELL-DYN® Ruby™, CELL-DYN® 3200, and CELL-DYN® 4000 systems (REF #01H73-01), commercially available from Abbott Laboratories.

The reference lysing agent used in this example was the CN-Free HGB/NOC Lyse for the CELL-DYN® Ruby™ and CELL-DYN® 3200 systems (REF #03H80-02), commercially available from Abbott Laboratories. This reference lysing agent for determination of hemoglobin contains at least one lysing component to rupture the membranes of red blood cells and at least one non-cyanide binding ligand for hemoglobin to form a stable hemoglobin-ligand complex for quantifying hemoglobin.

A ligand-free lysing agent was prepared using the formulation set forth in TABLE 1.

TABLE 1

| Component | Function | Quantity or measure |
|---|---|---|
| Water (D.I.) | Solvent | 965 mL |
| Decylamine oxide (Ammonyx® DO) | Lysing agent; component to break erythrocytes | 35 mL |
| Sodium Chloride | For adjustment of osmolality to desired level | 20.0 g |
| Hydrochloric Acid (Concentrated) | For adjusting pH to desired level | 4.2 mL |
| pH | | 3.0 ± 0.2 |
| Osmolality (mOsm) | | 980 ± 20 |

The following table shows the three samples that were prepared for this example.

TABLE 2

| Sample | Amount of whole blood (μL) | Amount of diluent (μL) | Amount of lysing agent (μL)/type of lysing agent |
|---|---|---|---|
| 1 | 10 | 2170 | 0/No lysing agent |
| 2 | 10 | 1420 | 750/reference |
| 3 | 10 | 1420 | 750/ligand free |

The three samples were incubated at a temperature of 40° C. for five (5) minutes before measurements were taken. Sample 1 contained 100% unlysed red blood cells. Samples 2 and 3 did not contain any red blood cells, on account of the extended incubation of red blood cells in strong lysing agents. As mentioned previously, a strong lysing agent is a lysing agent that can rupture membranes of red blood cells in a short period of time, e.g., less than 10 seconds. Examples of strong lysing agents include, but are not limited to, amine oxides and tetradecyl trimethyl ammonium bromide. Sample 2 contained hemoglobin-ligand complexes following the lysing step. Sample 3 contained free methemoglobin following the lysing step, i.e., no ligand was attached to the heme iron.

The analyses were conducted by measuring the absorbance spectrum of each sample from a wavelength of 500 to 610 nm, using the Helios Beta Single-Beam UV/Visible Spectrophotometer, commercially available from Thermo Scientific. FIG. 1 shows the spectra of the three samples of this example. The absorbance values at a wavelength of 555 nm were 1.306 for Sample 1, 0.249 for Sample 2, and 0.210 for sample 3. Therefore, a mixture of approximately 96% of Sample 3 and 4% of Sample 1 would yield an absorbance reading similar to that provided by the reference lysing agent (Sample 2). Alternatively, the component Sample 1 can be replaced by an appropriate sample that is rich in fragments of red blood cells.

A combination of free methemoglobin (greater than 50% of the composition) and unlysed red blood cells or fragments of red blood cells (less than 50% of the composition) resulting from a ligand-free lysing agent can match the performance of a reference lysing agent in a hemoglobin analysis.

Example 2

The purpose of this example is to demonstrate the possibility of formulating a ligand-free lysing agent by using combinations of lysing agents and adjusting final pH of the lysing agent in order to elevate absorbance values, with an elevated value of pH, or in order to reduce absorbance values, with a reduced value of pH.

Various components of a lysing agent, as well as different combinations of lysing agent and diluent, were investigated to optimize the method of hemoglobin analysis. More particularly, tetradecyl trimethyl ammonium bromide (TTAB) and amine oxide-based compounds, as well as the final pH of the lysing agent, were investigated.

A CELL-DYN® 3200 hematology analyzer, commercially available from Abbott Laboratories, was used in this example. The reference reagents used in this study were: CN-Free HGB/NOC Lyse (REF #03H80-02), WBC Lyse (REF #08H52-01), and Diluent/Sheath (REF #01H73-01). All reference reagents, intended for use for the CELL-DYN® Ruby and CELL-DYN® 3200 hematology analyzers, are commercially available from Abbott Laboratories.

The lysing agent for white blood cells used in this example was a low-osmolality lysing agent containing surfactant(s) and leuko-protecting agent(s). The final pH of the lysing agent for white blood cells was approximately 8.5. The final osmolality of the lysing agent for white blood cells was approximately 50 mOsm.

The diluent used in this example was based on phosphate buffered saline, and contained appropriate anti-coagulant(s), antimicrobial agent(s) and red blood cell sphering agent(s). The pH of the diluent was approximately 7.2. The osmolality of the diluent was approximately 312 mOsm.

The formulations for the ligand-free lysing agents for this example are shown in TABLE 3.

TABLE 3

| Formulation | Concentration of TTAB (% v/v) | Amine Oxide Compounds (% v/v) | | | pH |
| | | Lauramine oxide (Ammonyx® LO) | Decylamine oxide (Ammonyx® DO) | Myristamine oxide (Ammonyx® MO) | |
|---|---|---|---|---|---|
| 1 | 10 | | | | Unadjusted |
| 2 | 10 | 10 | | | Unadjusted |
| 3 | 10 | | 10 | | Unadjusted |
| 4 | 10 | | | 10 | Unadjusted |
| 5 | 10 | | 10 | | Lower to 3.0 |

The values of the concentration of hemoglobin (g/dL) are shown in TABLE 4.

TABLE 4

| Formulation | Sample 1 (hemoglobin, g/dL) | Sample 2 (hemoglobin, g/dL) | Sample 3 (hemoglobin, g/dL) | Control (Para 12® Plus N) |
|---|---|---|---|---|
| Reference | 14.57 | 14.02 | 13.48 | 12.53 |
| 1 | 15.73 | 15.28 | 14.60 | 13.45 |
| 2 | 14.85 | 14.43 | 13.83 | 12.83 |
| 3 | 14.55 | 14.15 | 13.53 | 12.15 |
| 4 | 14.75 | 14.38 | 13.78 | 12.60 |
| 5 | 13.03 | 12.52 | 11.90 | 11.20 |

This example shows that the use of a strong lysing agent or combinations of strong lysing agents in a ligand-free lysing agent can effectively lower the values of absorbance and concentration of hemoglobin (Formulations 2, 3, 4). This example also shows that lowering the pH of the ligand-free lysing agent can further destroy red blood cells, reduce the number of fragments of red blood cells, and lower the values of absorbance (Formulation 5).

This example demonstrates the possibility of formulating a ligand-free lysing agent by using combinations of ligand-free lysing agents and optimizing the pH value of the resulting ligand-free lysing agent in order to match reference absorbance values. In general, the pH can range from about 1 to about 12.

Example 3

The purpose of this example is to demonstrate that the values of concentration of hemoglobin determined with ligand-free lysing agents closely match well those values determined by reference lysing agents. This example utilized three samples of whole blood and one control sample at the normal level.

A CELL-DYN® 3200 hematology analyzer, commercially available from Abbott Laboratories, was used in this example.

The reference lysing agents were the same as those described in EXAMPLE 2.

The optimal formulation of the ligand-free lysing agent is shown in TABLE 1 of EXAMPLE 1. The lysing agent and diluent for white blood cells used to support the hemoglobin determination were the same as those described in EXAMPLE 2.

Comprehensive hematology assay results are shown in TABLE 5. In the table, "WBC" represents white blood cells (thousands per microliter), "NE" represents neutrophils (%), "LY" represents lymphocytes (%), "MO" represents monocytes (%), "EO" represents eosinophils (%), "BA" represents basophils (%), "RBC" represents red blood cells (millions per microliter), "HGB" represents hemoglobin (grams per deciliter), "HCT" represents hematocrit (%), "MCV" represents mean cell volume (femtoliters), "MCH" represents mean cell hemoglobin (picograms/cell), "MCHC" represents mean cell hemoglobin concentration (grams per deciliter), "RDW" represents red blood cell distribution width, "PLT" represents platelets (thousands per microliter), and "MPV" represents mean platelet volume (femtoliters).

A CELL-DYN® 3200 hematology analyzer, commercially available from Abbott Laboratories, was used in this example.

The reference reagents were the same as those described in EXAMPLE 2.

The optimized formulation of a ligand-free lysing agent is shown in TABLE 1 of EXAMPLE 1. The lysing agent and diluent for white blood cells used to support the lysing runs for the determination of hemoglobin were the same as those described in EXAMPLE 2.

Figure 2:
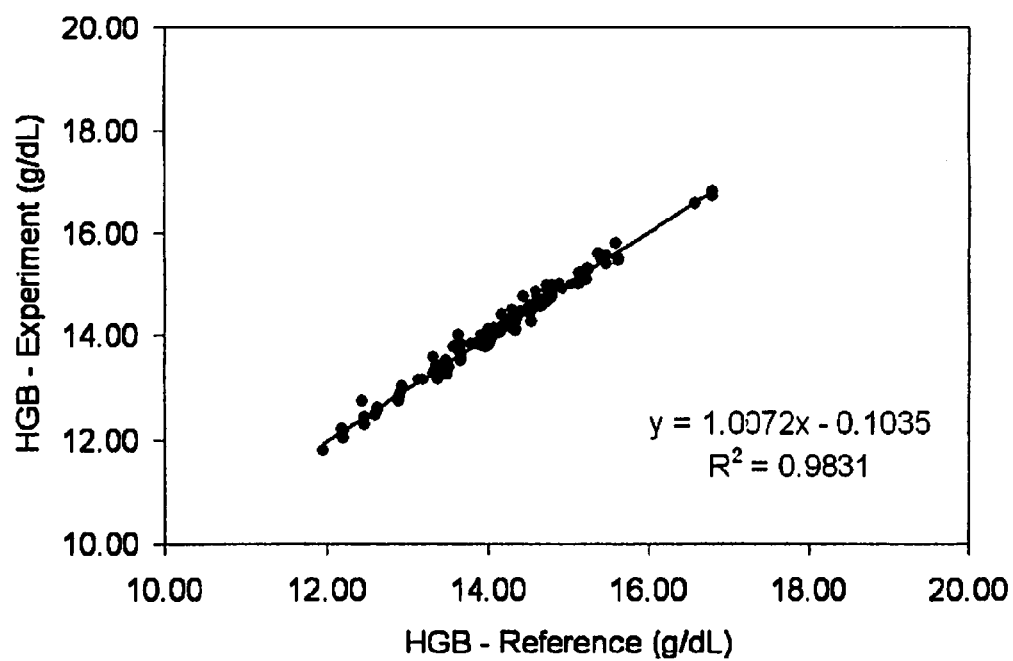
FIG. 2 is a graph illustrating the correlation between the values of concentration of hemoglobin determined by the method described herein and the values of concentration of hemoglobin determined by the CELL-DYN® 3200 hematology analyzer with reference reagents, as described in EXAMPLE 4.

A total of 128 fresh samples of whole blood were used in the analysis of hemoglobin with both reference lysing agent and the ligand-free lysing agent described herein. The values of the concentration of hemoglobin were measured and the biases in hemoglobin, i.e., $\Delta HGB$ ($HGB_{Expt}-HGB_{Ref}$), were calculated for all 128 samples. $HGB_{Expt}$ means concentration of hemoglobin as determined by the method described herein. $HGB_{Ref}$ means concentration of hemoglobin as determined by a reference method. The average bias was 0.00 g/dL (ranging from −0.28 to +0.38 g/dL). FIG. 2 shows the correlation in values of hemoglobin measured for all 128 samples. The best fit, based on linear regression, was $HGB_{Expt}=1.0072$ $HGB_{Ref}-0.1035$ ($R^2=0.9831$). This fit indicates excellent correlation between the ligand-free lysing agent described herein and the reference lysing agents for measuring values of hemoglobin in samples of whole blood.

TABLE 5

| | WBC | NE | LY | MO | EO | BA | RBC | HGB | HCT | MCV | MCH | MCHC | RDW | PLT | MPV |
|---|---|---|---|---|---|---|---|---|---|---|---|---|---|---|---|
| Sample of whole blood 1 | | | | | | | | | | | | | | | |
| Reference | 5.4 | 64.8 | 25.9 | 6.7 | 1.4 | 1.2 | 5.24 | 14.68 | 42.2 | 80.5 | 27.9 | 34.7 | 11.6 | 315 | 7.9 |
| Ligand-free lysing agent | 5.4 | 65.4 | 25.6 | 6.3 | 1.4 | 1.2 | 5.27 | 14.63 | 42.4 | 80.4 | 27.8 | 34.5 | 11.6 | 326 | 8.1 |
| Sample of whole blood 2 | | | | | | | | | | | | | | | |
| Reference | 8.9 | 68.1 | 22.3 | 6.8 | 2.3 | 0.6 | 4.73 | 13.10 | 39.5 | 83.5 | 27.7 | 33.2 | 12.6 | 203 | 10.9 |
| Ligand-free lysing agent | 8.9 | 67.9 | 21.7 | 7.2 | 2.3 | 0.9 | 4.72 | 13.15 | 39.2 | 83.0 | 27.9 | 33.6 | 12.7 | 212 | 10.8 |
| Sample of whole blood 3 | | | | | | | | | | | | | | | |
| Reference | 6.0 | 51.5 | 37.5 | 8.1 | 1.8 | 1.0 | 4.69 | 14.58 | 44.2 | 94.3 | 31.1 | 32.9 | 11.9 | 159 | 12.1 |
| Ligand-free lysing agent | 6.2 | 51.8 | 37.1 | 8.1 | 2.0 | 1.0 | 4.68 | 14.55 | 43.8 | 93.6 | 31.1 | 33.2 | 11.8 | 158 | 12.2 |
| Reference | 8.4 | 55.8 | 27.5 | 9.9 | 2.4 | 4.4 | 4.15 | 12.25 | 33.0 | 79.5 | 29.6 | 37.3 | 11.8 | 206 | 9.1 |
| Control sample (Para 12 ® Plus N) | 8.5 | 55.2 | 27.8 | 9.9 | 2.4 | 4.8 | 4.17 | 12.23 | 33.8 | 80.9 | 29.3 | 36.2 | 12.0 | 217 | 9.6 |

The results obtained through the use of the ligand-free lysing agent matched those obtained through the use of the reference lysing agent very well, in terms of recoveries of hemoglobin for the three samples of whole blood and the one control sample. The data reveal that the values determined by means of the ligand-free lysing agent matched the performance of the reference lysing agent very well. The ligand-free lysing agent did not adversely affect the other parameters of the samples.

Example 4

The purpose of this example is to demonstrate that the ligand-free lysing agent can function properly over a large number of samples of blood.

Example 5

The purpose of this example is to demonstrate that the ligand-free lysing agent described herein functions well for a large number of samples.

A Cell-Din®3200 hematology analyzer, commercially available from Abbott Laboratories, was used in this example.

The reference reagents were the same as those described in Example 2.

The optimized formulation of hemoglobin lysing agent is shown in TABLE 1 of EXAMPLE 1. The lysing agent and diluent for white blood cells used to support the lysing runs for determination of hemoglobin were the same as described in EXAMPLE 2.

Figure 3:
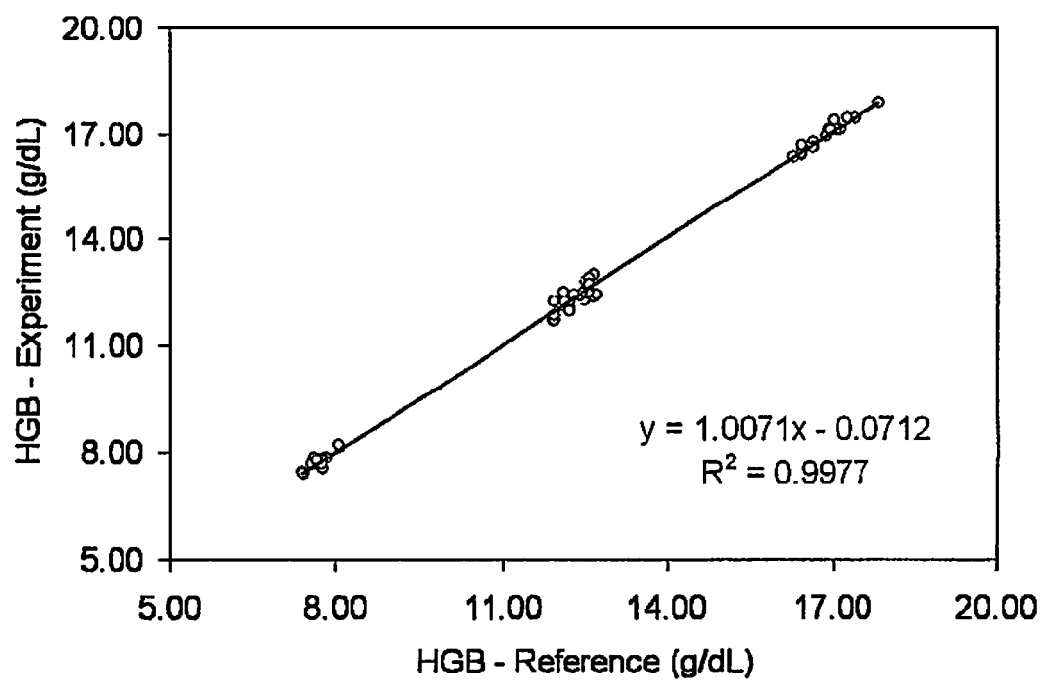
FIG. 3 is a graph illustrating is a graph illustrating the correlation between the values of concentration of hemoglobin determined by the method described herein and the values of concentration of hemoglobin determined by the CELL-DYN® 3200 hematology analyzer with reference reagents, as described in EXAMPLE 5.

A total of 67 control samples (Para 12® Plus) (Low, Normal and High) were used in the lysing runs with both reference lysing agent and the ligand-free lysing agent described herein. The values of concentration of hemoglobin were measured and the biases in hemoglobin, $\Delta$HGB ($HGB_{Expt}$–$HGB_{Ref}$), were calculated for all 67 samples. The average bias was +0.02 g/dL (ranging from −0.35 to +0.38 g/dL). FIG. 3 shows the correlation in values of hemoglobin measured for all 67 samples. The best fit, based on linear regression, was $HGB_{Expt}$=1.0071 $HGB_{Ref}$−0.0712 ($R^2$=0.9977). This fit indicates excellent correlation between the ligand-free lysing agent described herein and the reference lysing agent for measuring values of hemoglobin in samples of whole blood.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for analyzing a hemoglobin concentration in a sample of whole blood by means of an automated hematology analyzer and at least one ligand-free lysing agent, the method comprising:
    lysing a plurality of cells in the sample using at least one ligand-free lysing agent to produce a reaction mixture that comprises a plurality of ligand-free methemoglobin molecules; and
    measuring the concentration of the ligand-free methemoglobin molecules in the reaction mixture to determine the concentration of hemoglobin in the sample of whole blood.

2. The method of claim 1, wherein a level of turbidity is controlled in order to achieve accurate determination of the concentration of hemoglobin.

3. The method of claim 2, wherein measuring the concentration of the ligand-free methemoglobin molecules in the reaction mixture comprises determining an absorbance value of the reaction mixture at a specified wavelength.

4. The method of claim 3, wherein the wavelength ranges from about 540 nm to about 560 nm.

5. The method of claim 1, wherein the reaction mixture exhibits a molar absorptivity ($\epsilon$) of a reference lysing agent at a wavelength of measurement.

6. The method of claim 5, wherein the reference lysing agent is selected from the group consisting of cyanide, hydroxylamine HCl, imidazole, and derivatives thereof.

7. The method of claim 1, wherein all of the hemoglobin in the reaction mixture is in a ligand-free methemoglobin form.

8. The method of claim 1, wherein the concentration of the at least one ligand-free lysing agent determines a quantity of fragments of red blood cells remaining in the reaction mixture at the time of measurement of absorbance.

9. The method of claim 8, wherein a contribution to the absorbance of the reaction mixture from the quantity of fragments of red blood cells is represented by $A_{RBC\ fragments}$, where $$A_{RBC\ fragments} = (\epsilon(\text{met-Hb}) \times c \times l) - A_{Target}, \text{ wherein}$$

$A_{Target}$ represents the absorbance of a reference method;
$\epsilon$(met-Hb) represents the molar absorptivity of ligand-free methemoglobin;
c represents the concentration of ligand-free methemoglobin;
l represents the light pass length; and
$A_{RBC\ fragments}$ represents the contribution to the absorbance from the fragments of red blood cells.

10. The method of claim 1, wherein said at least one ligand-free lysing agent is selected from the group consisting of (1) quaternary ammonium salts, (2) tertiary ammonium salts, (3) quaternary amine oxides, (4) tertiary amine oxides, and (5) sodium dodecyl sulfate.

11. The method of claim 10, wherein the ligand-free lysing agent further comprises a non-ionic or an anionic surfactant other than sodium dodecyl sulfate.

12. The method of claim 10, wherein the ligand-free lysing agent further comprises a solvent.

13. The method of claim 12, wherein the ligand-free lysing agent further comprises a diluent.

14. The method of claim 10, wherein the ligand-free lysing agent comprises a first component and a second component, and wherein the first and second components are each selected from the group consisting of (1) quaternary ammonium salts, (2) tertiary ammonium salts, (3) quaternary amine oxides, (4) tertiary amine oxides, and (5) sodium dodecyl sulfate.

15. The method of claim 1, wherein the reaction mixture comprises a combination of ligand-free methemoglobin and fragments of red blood cells resulting from lysis of red blood cells and wherein a target absorbance of a reference lysing agent for determination of hemoglobin is matched.

16. The method of claim 15, wherein at least 75% the absorbance of the reaction mixture is contributed by ligand-free methemoglobin.

17. The method of claim 15, wherein at least 90% the absorbance of the reaction mixture is contributed by ligand-free methemoglobin.

18. The method of claim 15, wherein at least 95% the absorbance of the reaction mixture is contributed by ligand-free methemoglobin.

19. The method of claim 15, wherein less than 25% of fragments of red blood cells resulting from lysis of red blood cells contribute to absorbance of the reaction mixture.

20. The method of claim 15, wherein less than 10% of fragments of red blood cells resulting from lysis of red blood cells contribute to absorbance of the reaction mixture.

21. The method of claim 15, wherein less than 5% of fragments of red blood cells resulting from lysis of red blood cells contribute to absorbance of the reaction mixture.

22. The method of claim 1, wherein the at least one ligand-free lysing agent comprises at least one tertiary amine oxide or at least one tertiary ammonium salt.

23. The method of claim 22, wherein the concentration of the tertiary amine oxide or the tertiary ammonium salt ranges from about 0.01% to about 50%.

24. The method of claim 1, wherein the at least one ligand-free lysing agent comprises at least one quaternary amine oxide or at least one quaternary ammonium salt.

25. The method of claim 24, wherein the concentration of the quaternary amine oxide or the quaternary ammonium salt ranges from about 0.01% to about 50%.

26. The method of claim 1, wherein a final pH value of the reaction mixture is adjusted so that the absorbance of the reaction mixture matches the absorbance of a reference mixture.

27. The method of claim 26, wherein the final pH value of the reaction mixture ranges from about 1 to about 12 pH units.

* * * * *